United States Patent [19]

Berner et al.

[11] Patent Number: 4,968,140

[45] Date of Patent: Nov. 6, 1990

[54] MANUAL DEVICE FOR THE DETERMINATION OR MEASUREMENT OF PHOTOMETRIC DATA USING A MEASURING HEAD

[75] Inventors: Markus Berner, Niederhasli; Fortunat Schrämmli, Hausen; Lido Feri, Nussbaumen; Wilhelm H. Koch, Otelfingen, all of Switzerland

[73] Assignee: Gretag Aktiengesellschaft, Regensdorf, Switzerland

[21] Appl. No.: 300,928

[22] Filed: Jan. 24, 1989

[30] Foreign Application Priority Data

Feb. 2, 1988 [CH] Switzerland .......................... 362/88

[51] Int. Cl.[5] .................... G01N 21/01; G01D 3/32
[52] U.S. Cl. .................................. 356/244; 356/446; 356/328
[58] Field of Search ............... 356/244, 404, 406, 416, 356/418, 419, 443, 444, 445, 32 B; 350/446

[56] References Cited

U.S. PATENT DOCUMENTS

| | | |
|---|---|---|
| 3,244,062 | 4/1966 | Sweet . |
| 3,923,399 | 12/1975 | Brumley . |
| 3,982,824 | 9/1976 | Rambauske . |
| 4,025,200 | 5/1977 | Zeineh . |
| 4,053,235 | 10/1977 | Hampton et al. ............... 356/418 |
| 4,076,421 | 2/1978 | Kishner . |
| 4,078,858 | 3/1978 | Mast . |
| 4,093,991 | 6/1978 | Christie, Jr. et al. . |
| 4,645,350 | 2/1987 | Weidmann et al. ................ 356/446 |
| 4,756,619 | 7/1988 | Gerlinger et al. . |
| 4,802,763 | 2/1989 | Gerlinger et al. . |
| 4,865,456 | 9/1989 | Mast et al. . |

FOREIGN PATENT DOCUMENTS

| | | |
|---|---|---|
| 0242725 | 10/1987 | European Pat. Off. . |
| 3313668 | 10/1984 | Fed. Rep. of Germany . |
| 1527717 | 6/1968 | France . |
| 142240 | 12/1987 | Japan . |
| 2181265 | 4/1987 | United Kingdom . |

OTHER PUBLICATIONS

Nouvelles Graphiques, vol. 37, No. 2, Jan. 1987, "La Nature Connait Ses Imperfections", Macbeth y pallie.
Eine einfache Messanordnung zur photoelektrischen Spektrometrie moglichst kleiner Konzentrationen, M. Nordmeyer, Spectrochimica Acta, vol. 27B, No. 8, Aug. 1972, Pergamon Press (Northern Ireland).
Proceedings of the Society of Photo-Optical Instrumentation Engineers, vol. 240, "Periodic Structures, Gratings, Moire Patterns, and Diffraction Phenomena", Jun. 29-Aug. 1, 1980, San Diego, J. M. Lerner Diffraction Gratings Ruled and Hologaphic—A Review, pp. 82-88.
Unterscheiden Kleinste Differenzen, H. Hencke, Feb. 27, 1987, pp. 29-39.

*Primary Examiner*—Vincent P. McGraw
*Assistant Examiner*—S. A. Turner
*Attorney, Agent, or Firm*—Burns, Doane, Swecker & Mathis

[57] ABSTRACT

A manual device for the detection of photometric values on a printed product comprises a measuring head extruding from a housing into a measuring position. The measuring head is mounted together with its optical components on a measuring carriage, which may be displaced along the bottom of the housing by means of a drive motor between a rest position and a measuring position. The drive motor drives via a gear, a drive pulley and a grid axle for a monochromator. A sliding gear and a locking device are coordinated with the drive pulley, with the locking device immobilizing the measuring carriage precisely in the measuring position. The drive motor serves to displace the measuring carriage until the locking process essentially begins; and after this process, serves to rotate the grid axle.

14 Claims, 5 Drawing Sheets

MANUAL DEVICE FOR THE DETERMINATION OR MEASUREMENT OF PHOTOMETRIC DATA USING A MEASURING HEAD

BACKGROUND OF THE INVENTION

The invention relates to a manual device for the determination of photometric data. More specifically, the invention relates to a manual device to measure photometric data, which includes a support surface to be placed onto a flat measuring surface and a measuring head movably mounted in a housing in an essentially straight line manner and parallel to the support surface, the measuring head being capable of movement between a rest position in which a measuring diaphragm serving to position the manual device on the measuring surface is visible to the user, and a working position in which it covers the measuring diaphragm, the measuring head further being mounted on a motor-driven measuring carriage movably located in the housing of the manual device, with a drive motor being fastened to said measuring carriage, and with a drive pulley actuated by the drive motor and equipped with a crank pin, said drive pulley engaging a slide guide mounted stationarily in the housing.

A manual top view densitometer for the graphical industry is known from EP No. 171 360 A2 and makes it possible with the measuring head extended, to completely rotate a filter wheel twice, while the drive pulley cooperating with the sliding guide travels over an angle of only about 90°. The translation applied not only increases the rotating angle, but also enlarges the positioning error of the drive pulley, for which reason the known mechanical layout does not make it possible to carry out an accurate angular positioning of the filter wheel. The crank pin located at the drive pulley is permanently engaged in the slide guide, which has a specially adapted configuration.

SUMMARY OF THE INVENTION

Based on this state of the art, it is the object of the invention to provide a manual device of the aforementioned type, whereby both the accurate positioning of the measuring carriage and the precise determination of densitometric and/or colorimetric data are possible.

This object is attained according to the invention with a manual device for measuring photometric data wherein the drive of the measuring carriage is coupled with a shaft having a rotating position by which the wavelength range of the measuring head may be scanned, and wherein the crank pin may be rotated out of the stationary slide guide by beginning the measuring process.

In a practical exemplary embodiment of the invention, the shaft, which may be accurately set in its rotating position, is connected with the holder of the diffraction grid of a monochromator. The slide guide associated with the crank pin of the drive pulley consists of a guide groove provided in a stationary part, which is open at one end in the direction of the movement of the crank pin, so that the crank pin may be rotated out of engagement with the slide guide groove. It is possible in this manner to disengage the drive of the grid shaft of the monochromator from the drive of the measuring carriage.

In order to insure that the measuring carriage remains in a precise predetermined position when the crank pin is disengaged, a locking device actuated by the rotating position of the drive pulley, is provided. The locking device consists in an exemplary embodiment of the invention of a dual arm locking lever carrying a locking pin on one end that may be lowered into a stationary locking groove when a scanning pin provided at the opposite end passes through a switching curve located on the side opposite the crank pin of the drive pulley. Particularly advantageous forms of embodiments and further developments are set forth in the dependent claims.

BRIEF DESCRIPTION OF THE DRAWINGS

Other objects and advantages of the present invention will become apparent from the following detailed description of preferred embodiments as described in conjunction with the accompanying drawings in which:

FIG. 8 shows a view corresponding to FIG. 5, following the rotation of the crank pin from the slide guide groove, with the locking device snapped in.

DETAILED DESCRIPTION OF THE PREFERRED EMBODIMENTS

Figure 1:
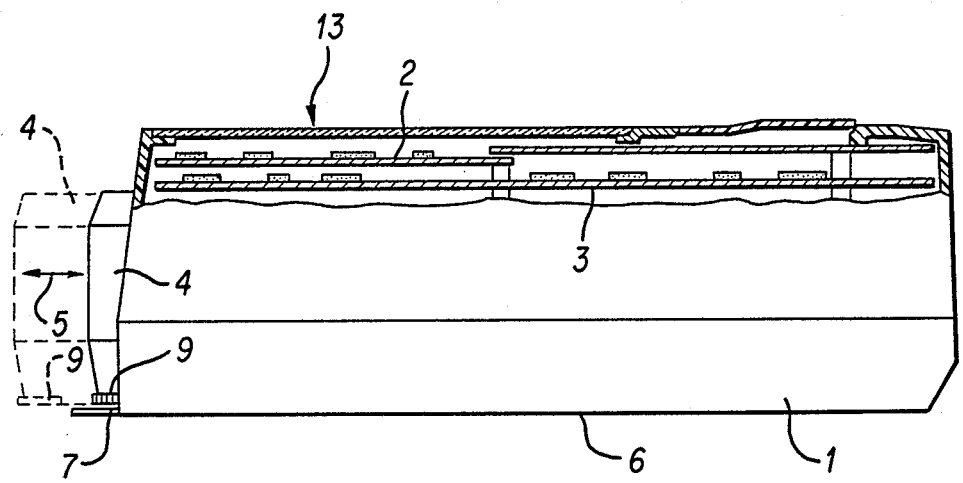
FIG. 1 shows a partial, cross-sectional lateral elevation of the manual device according to the invention.

The device shown in FIG. 1 in a lateral elevation and partially sectioned, corresponds in its external dimensions to a manual top densitometer and has a similar compact configuration. However, in contrast to a conventional densitometer the device shown in FIG. 1 permits the determination of densitometric values in addition to colorimetric data.

The manual device has a housing 1, in which one or several printed boards 2, 3 for a measured data processing and control logic are located as shown schematically in the upper part of the sectioned housing 1.

A measuring head 4 is protruding from the left hand lateral wall of the housing 1, said measuring head 4 being displaceable between a rest position shown in FIG. 1 by solid lines and a working position shown in FIG. 1 by a broken line, along the double arrow 5 parallel to the bottom 6 of the housing 1. In the retracted rest position, a sight plate 7 projects over the edge of the measuring head 4, which is seen with particular clarity in FIG. 2. The sight plate 7 has a measuring diaphragm 8 to indicate the position and size of the measuring spot of the measuring head 4 in the working position and to shield against scatter light.

Figure 2:
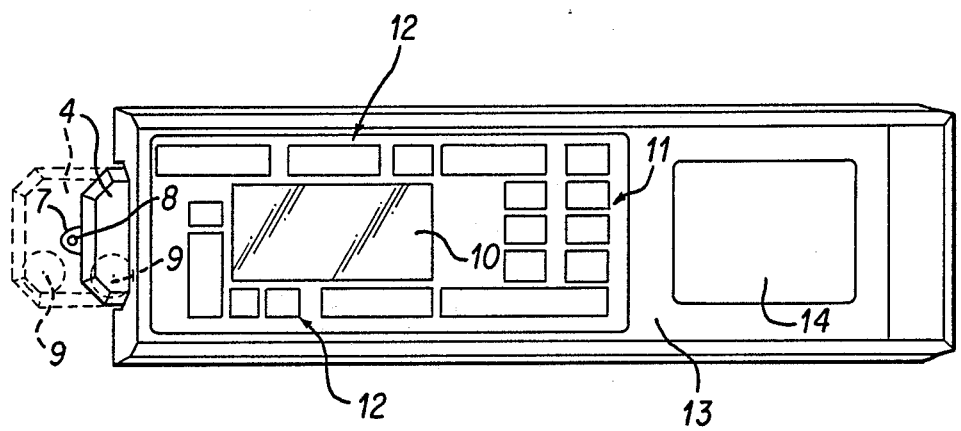
FIG. 2 shows a top elevation of the manual device.

When the measuring head 4 is moved from its rest position shown in FIGS. 1 and 2 into the working position shown by broken lines in FIGS. 1 and 2, the optically effective axis of the measuring head 4 passes exactly through the center of the measuring diaphragm 8.

The mechanical layout used for this purpose is described below with reference to FIGS. 3 to 8.

In FIGS. 1 and 2, a filter wheel drive 9 may further be seen, which engages a filter wheel provided in the measuring head 4 and which makes it possible to insert into the beam path of the measuring head 4 a polarizer to measure wet printed sheets, a D65 conversion filter for taking fluorescence into account, or a diaphragm without a filter. The filter wheel drive 9 thus has three positions which are set manually, but which may be displayed on a display field 10, for example a liquid crystal display.

The display field 10 also serves to indicate the measured values determined by the manual device in digital form or in the shape of spectra or bar diagrams. For the operation of the manual device, a row of keys of a keyboard 11 and several pointer fields 12 correlated with the display field 10 are located around the display 10. The display field 10, the keyboard and the pointer fields 12 are located on the top side 13 of a housing 1, while on the side facing away from the measuring head 4 a flat measuring key 14 is provided for the actuation of a measuring process.

The actuation of the measuring key 14 causes the measured data processing and control logic to move the measuring head 4 from its rest position into the working position, in order to detect by means of a spectral chamber with a diffraction grid provided inside the housing 1, the spectrum of the light reflected for example by a printed sheet upon which the manual device is resting, at the location of the measuring diaphragm 8. The reflection spectrum is processed by the measured data processing and control logic. Following the detection of the spectrum, the measuring head 4 returns into its rest position, until another measuring process is actuated by means of the measuring key 14.

Figure 3:
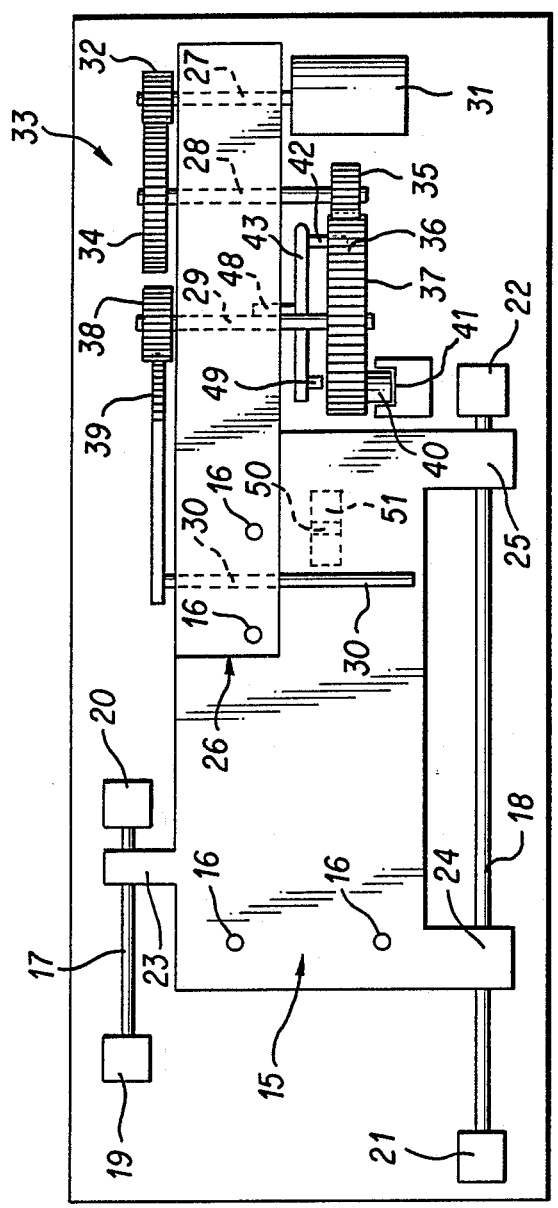
FIG. 3 shows an example of an embodiment of a measuring carriage and grid drive of the manual device in a rest position, in a top view.
Figure 4:
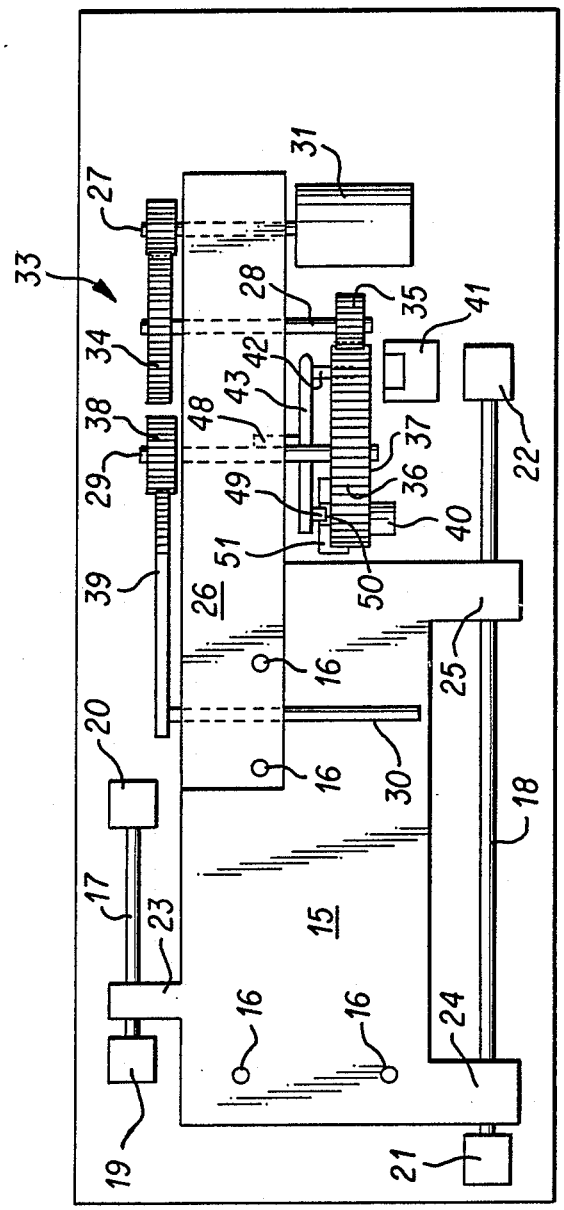
FIG. 4 shows a view corresponding to FIG. 3, in which the measuring carriage is in the measuring position.

The measuring head 4 is displaced by means of a measuring carriage 15 shown in FIGS. 3 and 4. The measuring carriage 15 is shown in FIGS. 3 and 4 without its optical and optoelectronic components which make the detection of the reflection spectrum possible. In FIGS. 3 and 4 merely a plurality of fastening holes 16 for the optical and optoelectronic components are seen.

The measuring carriage 15 is guided within the housing 1 in a longitudinally displaceable manner by means in the exemplary embodiment shown in FIGS. 3 and 4 of two guide rods 17, 18 extending between fastening posts 19 to 22. The measuring carriage 15 has a plurality of extension arms 23 to 25 in which sliding bushings are provided, whereby the measuring carriage 15 may be displaced with little friction between the rest position shown in FIG. 3 and the measuring position of FIG. 4 correlated with the working position of the measuring head 4.

On the essentially flat part of the measuring carriage 15 equipped with the extension arms 23 to 25, a support plate 26 is mounted at right angles, in which a motor shaft 27, a gear shaft 28, a drive shaft 29 and a grid shaft 30 are rotatably and stationarily fastened in the axial direction.

The grid shaft 30 protrudes into a spectral chamber, not shown, and serves to mount a holder for the diffraction grid of a monochromator for the spectral analysis of the light detected by the measuring head 4. Depending on the rotated position of the grid shaft, the monochromator is tuned to a light wavelength in the visible range. The visible light wave range is scanned by means of a drive motor 31, which drives both the grid and the measuring carriage.

The drive motor 31 is fastened to the right end of the bearing plate 26, which as seen in FIGS. 3 and 4, projects to the right, over the part of the measuring carriage 15 essentially parallel to the bottom 6 of the housing 1. The drive motor drives by means of the motor shaft 27 a first pinion 32 of the gear 33, which together with the gear wheel 34, forms the first reduction stage of the gear 33. The gear wheel 34 is connected fixedly in rotation with the drive shaft 28 and drives a second pinion 35, which fits into the outer teeth 36 of the drive pulley 37.

The drive pulley 37, together with the second pinion 35 and second reduction stage of the gear 33, forms and transmits by means of the drive shaft 29, a torque to the third reduction stage, which consists of a third pinion 38 and a tooth segment 39 fastened fixedly in rotation to the grid shaft 30 and making possible the pivoting of the grid shaft 30 between an initial angle and a terminal angle. To reduce the clearance of the teeth, the tooth segment 39 is prestressed by a spring, not shown. As the drive motor 31 drives the grid shaft 30 by means of a rigid tooth gear, the rotational position of the diffraction grid fastened to the grid shaft 30 or any other object, in particular a filter, may be accurately set relative to position.

The motor position must be known very accurately, as the position of the diffraction grid and thus of the spectral range detected depends on it. The drive motor 31 is a dc motor, the motor rpm of which is controlled by means of a phase lock loop, PLL. The nominal frequency is provided by a quartz of the microprocesser or of the measured data processing and control logic. The quartz frequency is subdivided by a timer in the processor. The actual frequency is provided by an incremental emitter on the drive motor 31 with 120 increments per revolution. It is assured in this manner that the drive motor 31 is rotating with quartz accuracy.

The specific type of the phase detector used, which is in the form of a synchronous automatic device, makes it further possible to reliably detect error situations, for example, a nonrecurring hang out of the PLL. For the absolute positional detection of the grid/measuring carriage drive, two light detectors or barriers, again not shown, are provided, one of which scans an emitter disk on the drive pulley, and the other an emitter disk on the motor shaft 27. The two emitter disks together make possible the determination of the absolute position of the measuring carriage 15 and the absolutely accurate recognition of the position of the drive motor 31. Those skilled in the art will readily see that it would not have been possible to perform both functions with a single emitter disk, as both the motor shaft 27 and the drive shaft 29 carry out more than one revolution per measuring run. At the drive shaft 29, the accuracy of the position detection is significantly less in view of the first and second reduction stages inserted and is not sufficient for the accuracy required for the manual device described.

As mentioned above, the drive motor 31 not only drives the grid shaft 30, but also displaces the measuring carriage 15 between the positions shown in FIGS. 3 and 4. On its side facing away from the support plate 26, which may be displaced together with the carriage 15, the drive pulley 37 is equipped with a crank pin 40, which may be rotated preferably on a ball bearing, in order to reduce friction losses. As seen in FIGS. 3 to 8, the crank pin 40 is located in the vicinity of the external circumference of the drive pulley 37 and makes possible the displacement of the measuring carriage 15 by twice the distance of the crank pin 40 from the center of the drive pulley 37.

The carriage path of the measuring carriage 15 for example amounts to 23 mm and the grid rotating angle for measuring is 14°.

Figure 5:
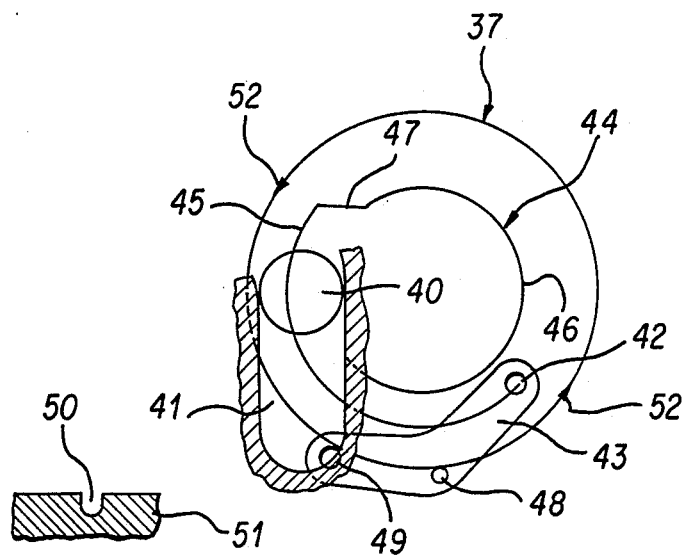
FIG. 5 shows a schematic view to visualize the kinematics of the measuring carriage drive and its locking in the rest position.

In its rest position shown in FIGS. 3 and 5, the crank pin 40 engages a straight line slide guide groove 41 located in a structural part stationarily connected with the bottom 6. When the drive motor 31 rotates the drive pulley 37 in the counterclockwise direction, as viewed from the surface of the drive pulley 37 equipped with the crank pin, the crank pin 40 initially slides in the slide groove 41 in the direction of the bottom 6, wherein a force is applied to the bearing plate 26 and the measuring carriage 15 by the drive shaft 29, whereby the measuring carriage 15 is displaced in FIG. 3 to the left.

When the drive shaft 29 is aligned with the slide groove 41, the crank pin 40 beings to slide in the slide groove 41 upwards, away from the bottom 6, whereby the measuring carriage 15 is further displaced toward the left into the position shown in FIG. 4. As soon as the crank pin 40 arrives at the height of the drive shaft 29, it disengages from the slide groove 41, which has an opening at this point. The open upper end of the slide guide groove 41 is chosen so that the motion of the measuring carriage 15 terminates toward the left, without the occurrence of a backward movement. In the direction of the bottom 6, the slide guide groove has a depth such that the crank pin 40 cannot impact the bottom of the slide guide groove 41. As seen in FIGS. 5 to 8, the opening of the slide guidegroove 41 is slightly rounded in the direction of the motion of the crank pin 40.

When the crank pin 40 exits on top from the opening of the slide guide groove 41, the force displacing the measuring carriage 15 is discontinued, but the drive pulley 37 may continue to rotate. This makes it possible to rotate the grid shaft 30 not only in an unnecessary but non-interfering manner during the displacement of the measuring carriage 15, but also to rotate the grid shaft 30—by means of the drive motor 31—when the measuring carriage has reached the extruded measuring position shown in FIG. 4. In this position it is also possible to control the drive motor in a manner such that the grid shaft 30 is rotated several times to the left and the right, in order to multiply scan a spectral range. As during this time the crank pin 40 is no longer engaging the slide guide groove 41, the measuring carriage 15 is not affected by the drive motor 31. However, to exclude other extraneous effects on the position of the measuring carriage 15, a locking device is provided as described below. If the measuring carriage 15 is to return from its measuring position shown in FIG. 3, the drive motor 31 is operated by the data processing and control logic in the reverse direction, until the drive pulley 37, which now is rotating in the clockwise direction, again engages with its crank pin 40 the slide guide groove 41 and returns the measuring carriage 15 into its rest position shown in FIG. 3, after about one-half revolution. The above-described process takes places exactly in the inverse order.

In the rest position, the position of the measuring carriage 15 is stable, as the crank pin 40 is at dead center and additional support is provided by a scanning pin 42 fastened to a locking lever 43 and engaging a control groove 44 located on the side of the drive pulley 37 facing away from the crank pin. The control groove 44 has the configuration seen in FIGS. 5 to 8 and consists of a first control curve 45 with a larger diameter and a second control curve 46 with a smaller diameter. The first control curve 45 extends over an angle of about 180°, while the second control curve covers an angle of about 270°. Between the first control curve 45 and the second control curve 46 a switching curve 47, bridging over a rotating angle of a few degrees, is provided.

When the scanning pin 42 is moving in the control groove 44 along the first control curve 45, the switching curve 47 and the second control curve 46, it is at a first determined distance over the first control curve and a second predetermined distance over the second control curve 46. The distance variation during the passage of the switching curve 47 is used to lock the measuring carriage 15 in the measuring position, as long as the crank pin 40 is not engaging the slide guide groove 41 in the manner shown in FIGS. 4 and 8.

The scanning pin 42 is located in the exemplary embodiment shown in the drawing at the right end of the locking lever 43. Persons skilled in the art will readily recognize that a configuration in which the left end of the locking lever 43 is equipped with the scanning pin 42 is also possible. The locking lever 43 is rotatably fastened on a lever axle 48, which in turn is fastened to the bearing plate 26. At the end facing the scanning pin 42 the dual ar locking lever 43 has a locking pin 49, which may be lowered or raised during the passage of the switching curve 47 by the scanning pin 42.

It is seen in FIGS. 4, 6, 7 and 8 that the locking pin 49 is provided with a locking groove 50 located in a locking piece 51 at the point wherein the locking pin 49 is located when the scanning pin 42 runs through the switching curve 47.

FIGS. 5 to 8 show the kinematics of the measuring carriage drive and its locking device in a summary manner.

Figure 6:
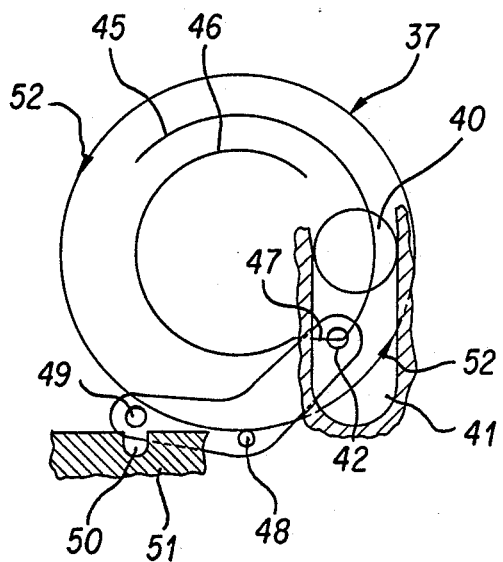
FIG. 6 shows a view corresponding to FIG. 5 at the end of the measuring carriage advance.

In FIG. 5, the scanning pin 42 supported against the onset of the first control curve 45 and the locking lever 43 with the locking pin 49 raised, are seen. The crank pin 40 is at the upper end of the slide guide curve 41. By rotating the schematically indicated drive pulley 37 in the direction of the arrows 52, the drive pulley and the other structural parts fastened to the measuring carriage 15 are shifted to the left until, following a revolution of the drive pulley 37 by 180°, the position shown in FIG. 6 is attained. During the rotation of the drive pulley 37, the grid shaft 30 has also been rotated, but the associated spectral range is outside the measuring range, so that this rotation has no effect and does not interfere.

Beginning with the view of FIG. 6, the locking lever 43 pivots in the counterclockwise direction around the lever axle 48, while the scanning pin 42 slides along the switching curve 47, which may be realized by a groove or another type of stop in the drive pulley or mechanically on the drive pulley.

Figure 7:
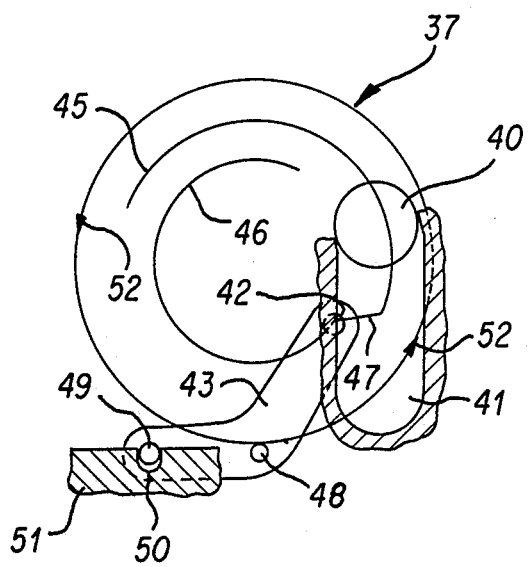
FIG. 7 shows a view corresponding to FIG. 5, after locking the measuring carriage.

When the scanning pin 42 has reached the transition between the switching curve 47 and the second control curve 46, the locking pin 49 is lowered in the manner shown in FIG. 7. In the process, the locking pin 49 engages the locking groove 50 in the stationary locking piece 51. The rotating position of the grid shaft 30 associated with FIG. 7 corresponds to the onset of the measuring range to be scanned by the diffraction grid. By snapping the locking pin 49 into the locking groove 50, it is assured that during the scanning the measuring carriage 15 remains stationary until the measurement is completed.

Figure 8:
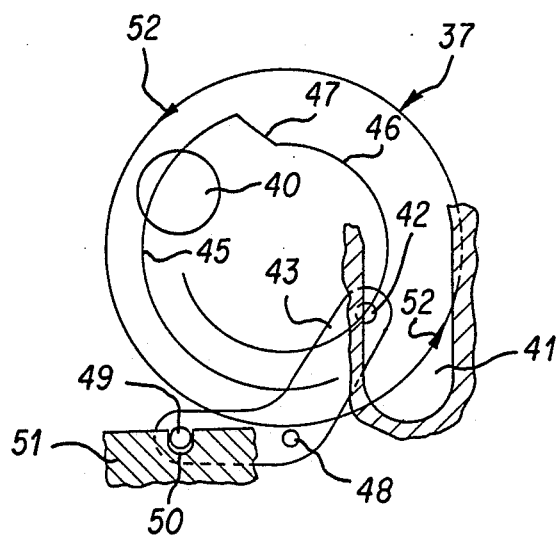

While in FIG. 7, the crank pin 40 is just leaving the slide guide groove 41, in FIG. 8 the crank pin 40 is entirely outside the slide guide groove 41. The measuring carriage 15 is now immobilized exclusively by the aforedescribed locking device and the drive motor 31 merely serves to rotate the grid shaft 30. It is seen in the drawings that beginning with FIG. 7, the drive pulley 37 may be rotated by more than 180°, wherein however, the angle of rotation is strongly reduced by the third reduction stage before it is used to precisely rotate the grid shaft 30 by means of the tooth segment 39.

The foregoing discussion shows that the measuring carriage 15 is moved into the measuring position by the drive motor 31 during each measurement. It remains stationary in this position until the measurement is carried out. In the course of the measurement, the diffraction grid rotates, while the measuring carriage 15 is stationary. The diffraction grid already rotates during the advance of the measuring carriage, but this represents no interference. Both in the measuring and in the rest position the measuring carriage 15 is being held fixedly and cannot be unintentionally inserted into or removed from the manual device. The gear 33 makes an extremely exact drive of the grid possible, with a grid rotating angle of, for example 14°.

The drive principle described above makes it possible to precisely drive the diffraction grid and the measuring carriage 15 by means of a single drive motor 31.

It will be appreciated by those of ordinary skill in the art that the present invention can be embodied in other specific forms without departing from the spirit or essential characteristics thereof. The present disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Manual device to measure photometric data comprising:
    a support surface to be placed onto a flat measuring surface;
    a measuring head movably mounted in a housing in an essentially straight line manner and parallel to said support surface, said measuring head being capable of movement between a rest position in which a measuring diaphragm serving to position the manual device on the measuring surface is visible to a user, and a working position in which the measuring head covers said measuring diaphragm, said measuring head further being mounted on a motor-driven measuring carriage movably located in the housing of the manual device;
    a drive motor being fastened to said measuring carriage for movement therewith;
    a drive pulley actuated by the drive motor for moving said carriage, said drive pulley being equipped with a crank pin for engaging a slide guide mounted stationarily in the housing, the crank pin being rotated out of the stationary slide guide at a beginning of a measuring process; and,
    a rotating shaft coupled with the drive motor of said measuring carriage by which the wavelength range of the measuring head may be scanned.

2. Manual device according to claim 1, wherein rotation of the crank pin out of the stationary slide actuates a locking device to immobilize the measuring carriage.

3. Manual device according to claim 2, wherein the rotating shaft is connected with a diffraction grid holder of a monochromator.

4. Manual device according to claim 3, wherein the drive pulley is driven by the drive motor via a gear with two reduction stages.

5. Manual device according to claim 4, further comprising:
    a first sensor disk mounted on the motor shaft;
    a second sensor disk mounted on a drive shaft carrying the drive pulley; and,
    light detector means for scanning each of said first and second disks to determine the position of the measuring carriage and the rotating shaft.

6. Manual device according to claim 5, wherein the drive motor is a dc motor, the rpm of which is regulated by means of a PLL circuit, with a nominal frequency being set by a quartz of a microprocessor of data processing and control logic and an actual frequency being provided by an incremental emitter on the drive motor.

7. Manual device according to claim 6, wherein the crank pin is rotatably mounted in the vicinity of the circumference of the drive pulley, said circumference being equipped with external toothing.

8. Manual device according to claim 7, wherein the slide guide comprises a channel extending essentially at right angles to said support surface.

9. Manual device according to claim 8, wherein the slide guide further comprises an opening slightly curving in a direction of motion of the crank pin at an end of the slide guide facing away from said support surface.

10. Manual device according to claim 2, wherein the locking device comprises a dual arm locking lever, which at one end carries a scanning pin engaging a control groove located on a side of the drive pulley opposite a side bearing the crank pin, while the other end of the locking lever is equipped with a locking pin that may be lowered into a locking groove fixedly connected with the support surface.

11. Manual device according to claim 10, wherein the control groove comprises a switching curve connecting a first control curve having a larger diameter, with a second control curve having a smaller diameter, said switching curve connecting said first and second control curves at a point where the scanning pin is located when the crank pin is about to leave the slide guide.

12. Manual device for the detection of photometric data comprising:
    a support surface to be placed on a flat measuring surface;
    a measuring head movably mounted between a rest position and a working position;
    a measuring carriage engaged with said measuring head;
    a drive motor in a housing of the manual device for displacing said measuring head between said rest and said working position, said drive motor being equipped with a gear coordinated with the measuring carriage to drive the measuring carriage; and,
    a further gear engaged by said drive motor to rotate a shaft connected with a diffraction grid of a tunable monochromator.

13. Manual device according to claim 1, wherein the slide guide comprises a channel extending essentially at right angles to said support surface.

14. Manual device according to claim 13, where the slide guide further comprises an opening slightly curving in a direction of motion of the crank pin at an end of the slide guide facing away from said support surface.

* * * * *